US012778897B2

(12) United States Patent
Leong et al.

(10) Patent No.: US 12,778,897 B2
(45) Date of Patent: Nov. 3, 2026

(54) BIO-MICROBUR THERAPEUTIC DELIVERY PLATFORM

(71) Applicant: The Trustees of Columbia University in the City of New York, New York, NY (US)

(72) Inventors: Kam W. Leong, New York, NY (US); Letao Yang, New York, NY (US); Yuefei Zhu, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 184 days.

(21) Appl. No.: 18/516,772

(22) Filed: Nov. 21, 2023

(65) Prior Publication Data

US 2025/0144018 A1 May 8, 2025

Related U.S. Application Data

(63) Continuation of application No. PCT/US2022/030383, filed on May 20, 2022, and a continuation of application No. PCT/US2022/030224, filed on May 20, 2022.

(60) Provisional application No. 63/191,759, filed on May 21, 2021, provisional application No. 63/191,586, filed on May 21, 2021.

(51) Int. Cl.

| | |
|---|---|
| ***A61K 9/50*** | (2006.01) |
| ***A61K 9/00*** | (2006.01) |
| ***A61K 9/14*** | (2006.01) |
| ***A61K 9/51*** | (2006.01) |
| ***A61K 45/06*** | (2006.01) |
| ***C01G 45/024*** | (2025.01) |

(52) U.S. Cl.

CPC ............ *A61K 9/501* (2013.01); *A61K 9/0092* (2013.01); *A61K 9/143* (2013.01); *A61K 9/5115* (2013.01); *A61K 9/513* (2013.01); *A61K 45/06* (2013.01); *C01G 45/024* (2025.01)

(58) Field of Classification Search

CPC .... A61K 9/501; A61K 9/143; A61K 9/51113; A61K 45/06; A61K 9/0092; A61K 9/513

See application file for complete search history.

(56) References Cited

U.S. PATENT DOCUMENTS

| | | | |
|---|---|---|---|
| 2008/0175915 | A1 | 7/2008 | Kim |
| 2008/0241262 | A1 | 10/2008 | Lee |
| 2014/0194479 | A1 | 7/2014 | Schmauss |
| 2015/0320694 | A1 | 11/2015 | Gu |
| 2019/0167698 | A1 | 6/2019 | Cashman |
| 2019/0275195 | A1 | 9/2019 | Leibler |
| 2020/0214989 | A1 | 7/2020 | Zhou |

FOREIGN PATENT DOCUMENTS

| | | |
|---|---|---|
| CN | 101935066 | 1/2011 |
| CN | 106495232 | 3/2017 |
| CN | 106882811 | 6/2017 |
| CN | 105645459 | 7/2017 |
| CN | 110917121 | 3/2020 |
| JP | 2007238424 | 9/2007 |

OTHER PUBLICATIONS

Kurakula et al. J.Drug Deliv. Sci Technol 2020 2(60).*

Zhang et al. (Applied Bio Materials 2020 3 4514-4521).*

Al-Jumah KA, Qureshi NA Impact of pharmacist interventions on patients' adherence to antidepressants and patient-reported outcomes: a systematic review. Patient Prefer Adherence 2012;6:87-100.

Alwan S, Friedman JM, Chambers C. Safety of Selective Serotonin Reuptake Inhibitors in Pregnancy: A Review of Current Evidence. CNS Drugs 2016.

Andrade SE, Raebel MA, Brown J, et al. Use of antidepressant medications during pregnancy: a multisite study. Am J Obstet Gynecol 2008; 198: 194 e1-5.

Ansorge MS, Morelli E, Gingrich JA. Inhibition of serotonin but not norepinephrine transport during development produces delayed, persistent perturbations of emotional behaviors in mice. J Neurosci 2008;28:199-207.

Ansorge MS, Zhou M, Lira A, et al. Early-life blockade of the 5-HT transporter alters emotional behavior in adult mice. Science 2004;306:879-81.

(Continued)

*Primary Examiner* — Shirley V Gembeh

(74) *Attorney, Agent, or Firm* — Fuller IP Law, LLC; Scott H. Blackman

(57) ABSTRACT

The bio-microbur therapeutic delivery platform is a three-dimensional (3D)-oriented nanoneedle platform shaped like a microscale version of a fruit bur. The bio-microbur may be used for drug delivery and other biological applications, including without limitation delivery of oral vaccines or other oral biologics. Similar to a fruit bur's ability to adhere to different surfaces, the bio-microbur therapeutic delivery platform adheres to biological tissue, cell membranes, and biological gels. The bio-microbur therapeutic delivery platform includes a core and a plurality of nanoneedles secured to the core and extending outwardly therefrom, adapted for carrying and delivering a therapeutic agent. The treating agent may be an SSRI, such as fluoxetine.

18 Claims, 13 Drawing Sheets

(56) References Cited

OTHER PUBLICATIONS

Apter-Levy Y, Feldman M, Vakart A, et al. Impact of maternal depression across the first 6 years of life on the child's mental health, social engagement, and empathy: The moderating role of oxytocin. Am J Psychiatry 2013; 170: 1161-8.

Bao et al, "A two-step hydrothermal route for synthesis hollow urchin-like ZnO microspheres", Ceramics International, Elsevier, Amsterdam, NL, (Mar. 22, 2016), vol. 42, No. 8, doi:10.1016/J.CERAMINT.2016.03.164, ISSN 0272-8842, pp. 10289-1.

Bassotti G. Motions and emotions: the treatment of depression causes constipation. Neurogastroenterol Motil 2000; 12: 113-5.

Brody DJ, Pratt LA, Hughes JP. Prevalence of Depression Among Adults Aged 20 and Over: United States, 2013-2016. NCHS Data Brief 2018: 1-8.

Dai et al., "Biocompatibility of Defect-Related Luminescent Nanostructured and Microstructured Hydroxyapatite", Biol Trace Elem Res, (Oct. 14, 2014), vol. 162, doi: 10.1007/s12011-014-0151-0, pp. 158-167, XP035376548.

El Marroun H, White T, Verhulst FC, et al. Maternal use of antidepressant or anxiolytic medication during pregnancy and childhood neurodevelopmental outcomes: a systematic review. Eur Child Adolesc Psychiatry 2014;23:973-92.

Gaynes BN, Gavin N, Meltzer-Brody S, et al. Perinatal depression: prevalence, screening accuracy, and screening outcomes. Evid Rep Technol Assess (Summ) 2005:1-8.

Gentile S. The safety of newer antidepressants in pregnancy and breastfeeding. Drug Saf 2005;28: 137-52.

Gollan JK, Fava M, Kurian B, et al. What are the clinical implications of new onset or worsening anxiety during the first two weeks of SSRI treatment for depression? Depress Anxiety 2012;29:94-101.

Hendrick V, Stowe ZN, Altshuler LL, et al. Placental passage of antidepressant medications. Am J Psychiatry 2003; 160:993-6.

Jacobsen JPR, Krystal AD, Krishnan KRR, et al. Adjunctive 5-Hydroxytryptophan Slow-Release for Treatment-Resistant Depression: Clinical and Preclinical Rationale. Trends Pharmacol Sci 2016;37:933-944.

Malm H, Brown AS, Gissler M, et al. Gestational Exposure to Selective Serotonin Reuptake Inhibitors and Offspring Psychiatric Disorders: A National Register-Based Study. J Am Acad Child Adolesc Psychiatry 2016;55:359-66.

Margolis KG, Li Z, Stevanovic K, et al. Serotonin transporter variant drives preventable gastrointestinal abnormalities in development and function. J Clin Invest 2016; 126:2221-35.

Marken PA, Munro JS. Selecting a Selective Serotonin Reuptake Inhibitor: Clinically Important Distinguishing Features. Prim Care Companion J Clin Psychiatry 2000;2:205-210.

McVey Neufeld KA, Bienenstock J, Bharwani A, et al. Oral selective serotonin reuptake inhibitors activate vagus nerve dependent gut-brain signalling. Sci Rep 2019;9: 14290.

National Comorbidity Survey (NCS).. https://www.hcp.med.harvard.edu/ncs/index.php, Harvard Medical School, 2007, all enclosed pages cited.

Nijenhuis CM, Horst PG, Berg LT, et al. Disturbed development of the enteric nervous system after in utero exposure of selective serotonin re-uptakeinhibitors and tricyclic antidepressants. Part 1: Literature review. Br J Clin Pharmacol 2012;73:16-26.

Nijenhuis CM, ter Horst PG, van Rein N, et al. Disturbed development of the enteric nervous system after in utero exposure of selective serotonin re-uptake inhibitors and tricyclic antidepressants. Part 2: Testing the hypotheses. Br J Clin Pharmacol 2012; 73:126-34.

O'Connor TG, Monk C, Burke AS. Maternal Affective Illness in the Perinatal Period and Child Development: Findings on Developmental Timing, Mechanisms, and Intervention. Curr Psychiatry Rep 2016; 18:24.

Sie SD, Wennink JM, van Oriel JJ, et al. Maternal use of SSRIs, SNRIs and NaSSAs: practical recommendations during pregnancy and lactation. Arch Dis Child Fetal Neonatal Ed 2012;97:F472-6.

Sinclair LI, Christmas OM, Hood SD, et al. Antidepressant-induced jitteriness/anxiety syndrome: systematic review. Br J Psychiatry 2009; 194:483-90.

Tanoshima R, Bournissen FG, Tanigawara Y, et al. Population PK modelling and simulation based on fluoxetine and norfluoxetine concentrations in milk: a milk concentration-based prediction model. Br J Clin Pharmacol 2014;78:918-28.

Thibaut F. Anxiety disorders: a review of current literature. Dialogues Clin Neurosci 2017; 19:87-88.

Trivedi MH, Rush AJ, Wisniewski SR, et al. Evaluation of outcomes with citalopram for depression using measurement-based care in STAR*D: implications for clinical practice. Am J Psychiatry 2006; 163:28-40.

Twenge JM, Joiner TE. U.S. Census Bureau-assessed prevalence of anxiety and depressive symptoms in 2019 and during the 2020 COVID-19 pandemic. Depress Anxiety 2020;37:954-956.

Yonkers KA, Blackwell KA, Glover J, et al. Antidepressant use in pregnant and postpartum women. Annu Rev Clin Psychol 2014;10:369-92.

* cited by examiner

BIO-MICROBUR THERAPEUTIC DELIVERY PLATFORM

This application is a continuation of international application no. PCT/US2022/030383, filed on May 20, 2022, entitled "Bio-Microbur Therapeutic Delivery Platform" (Inventors Kam W. Leong, Letao Yang, and Yuefei Zhu), which claims priority to U.S. Provisional Application No. 63/191,586, filed on May 21, 2021, and to U.S. Provisional Application No. 63/191,759, filed on May 21, 2021. This application is also a continuation of international application no. PCT/US2022/030224, filed on May 20, 2022, entitled "Compositions and Methods for Treating Depression and Anxiety" (Inventors Kara Margolis, Mark Ansorge, Kam W. Leong, Letao Yang, and Yuefei Zhu), which claims priority to U.S. Provisional Application No. 63/191,586, filed on May 21, 2021, and to U.S. Provisional Application No. 63/191,759, filed on May 21, 2021. All of the above are herein incorporated by reference in their entireties.

GOVERNMENT LICENSE RIGHTS

This invention was made with government support under W81XWH-17-1-0166 awarded by the United States Army Medical Research and Development Command (USAMRDC), and DE029951 awarded by the National Institutes of Health. The government has certain rights in the invention.

TECHNICAL FIELD

The disclosure of the present patent application relates to vehicles for targeted delivery of pharmaceuticals and other therapeutic agents, and particularly to a delivery platform with a bur-like configuration.

BACKGROUND

Maximizing drug efficacy on target tissues and organs while minimizing side effects on healthy body parts is crucial for ensuring efficient and safe treatment using medicinal products. For this purpose, having the ability to regulate the biodistribution of drugs in a precise and spatiotemporally controllable manner is highly desirable. Conventional drug administration approaches based on the injection of free drugs have often led to rapid clearance and uncontrollable diffusion of the drugs, thus requiring highly specialized methods for drug delivery.

Targeted drug delivery has been realized using nano/micro-materials as delivery vehicles, where drug biodistribution can be modulated by modulating surfaces, sizes, compositions, and shapes of the nano/micro-materials. However, presently used nano/micro-materials for this purpose are typically unsatisfactory, particularly for the treatment of diseases undergoing dynamic and complex microenvironmental changes. As a result, the frequency of failure of such materials in clinical trials is remains large. Although nano/micro-materials with greater structural complexities may convey more sophisticated and dynamic regulation of drug biodistribution, such complex structures have received minimal investigation with regard to drug delivery and other biological applications, despite their promise. It would be particularly desirable to be able to overcome the inadequate retention of delivery vehicles to target tissues and organs after administration found in the presently available nano/ micro-material delivery vehicles. Thus, a bio-microbur therapeutic delivery platform solving the aforementioned problems is desired.

SUMMARY

The bio-microbur therapeutic delivery platform is a three-dimensional (3D)-oriented nanoneedle platform having a shape simulative of a microscale version of a fruit bur (also spelled burr). The bio-microbur may be used for drug delivery and other biological applications. Similar to the ability of the fruit bur to adhere to many different types of surfaces (e.g., fur, ground and plants), the bio-microbur therapeutic delivery platform has superior retention to biological tissue (e.g., pig intestines), cell membranes (e.g., macrophage membranes), and biological gels (e.g., alginate hydrogels), when compared to conventional delivery vehicles such as nanoparticles and microparticles.

The bio-microbur therapeutic delivery platform includes a core and a plurality of nanoneedles secured to a surface of the core and extending outwardly therefrom. The plurality of nanoneedles are adapted for carrying and delivering a therapeutic agent. The core and the plurality of nanoneedles may be, for example, coated with the therapeutic agent. Alternatively, or used in combination with the previous example, the core may be hollow for carrying the therapeutic agent. The bio-microbur therapeutic delivery platform and the therapeutic agent may be delivered to the patient through injection or oral delivery, and may be formed from a biodegradable material to facilitate delivery and/or safe removal of the microburs.

The core and the plurality of nanoneedles may also each be formed from a metal oxide, such as, but not limited to, manganese oxide ($MnO_2$), zinc oxide (ZnO), gold (Au), silicon dioxide ($SiO_2$) or titanium oxide ($TiO_2$), or any combination of these compounds. Additionally, the metal oxide may be doped with a functional agent, such as, but not limited to, silver, which has antimicrobial properties; iron, which may be used in imaging and the like; selenium; aluminum; or a transition metal.

As a further alternative, the metal oxide may be functionalized with a surface conjugate to assist in attaching the bio-microbur therapeutic delivery platform to a cell membrane, biological gel or the like. A non-limiting example of such a surface conjugate is (3-aminopropyl)triethoxysilane (APTES). As an additional alternative, the metal oxide may be coated with a functional agent to increase adhesion between the bio-microbur therapeutic delivery platform and a cell membrane, biological gel or the like, such as, but not limited to, polyethylenimine (PEI), dextran, alginate, pullulan, hyaluronic acid, polyethylene glycol, a β-glucan, or chitosan.

In oral administration, the bio-microbur therapeutic delivery platform and the therapeutic agent may be delivered to the patient, for example, in a gelatin capsule, integrated into a hydrogel or the like. The coating or container, such as a gelatin capsule, may be intended for example, to protect the microbur delivery agent from exposure to the high stomach pH, and to release the microburs once the formulation passes through the stomach to the intestines or other high pH environment. When injected, the bio-microbur therapeutic delivery platform may be delivered in a suitable liquid carrier prior to injection in order to facilitate delivery to the target tissue, for example a cell membrane, such as that of a macrophage or a T cell. The vehicle and mode of delivery to a particular intended target tissue or target cells will be readily designed to facilitate delivery of the microburs to that target, so as to avoid premature release of the microburs which could result in adherence to non-target tissue or cells.

As a non-limiting example, manganese-based bio-microburs may be prepared by adding $Mn(CH_3COOH)_2 \cdot 4H_2O$ to $(NH_4)_2S_2O_8$ to form a first solution. Sulfuric acid is added to the first solution to form a second solution, and the second solution is heated to form a precipitate of bio-microburs, which are then extracted and washed. To dope the bio-microburs with silver, aluminum, iron, etc., the nitrate salts of the dopants may be added with the $Mn(CH_3COOH)_2 \cdot 4H_2O$ in the initial step. To modulate the size, shape, and structure of the bio-microburs, or the release rate of the treating agent, the concentrations of the precursors, the heating temperature and the time of heating may all be varied. For a non-limiting example, the time of heating may be a period of 0.5 hours, 1 hour, 2 hours, 3 hours, 4 hours, 5 hours, 6 hours, 7 hours, 8 hours, 9 hours, 10 hours, 11 hours, 12 hours, or 24 hours.

As another non-limiting example, zinc-based bio-microburs may be prepared by adding an aqueous solution of $Zn(CH_3COOH)_2 \cdot 2H_2O$ to an aqueous solution of NaOH to form a solution. The solution is heated to form a precipitate of bio-microburs, and the bio-microburs are then extracted, washed, and dried.

One embodiment provides a bio-microbur delivery platform comprising a core with a plurality of nanoneedles secured to the core surface and extending outward from the core, where the nanoneedles are adapted for carrying and delivering a therapeutic agent. The core and the nanoneedles may optionally comprise a biodegradable material. The core may optionally be spherical, and the nanoneedles optionally may have an average length of about 10 nm to about 10,000 nm. The therapeutic agent may optionally be an oral vaccine or another oral biologic agent. For example, the therapeutic agents can be genetic materials such as mRNAs, DNAs, or siRNAs. The therapeutic agents can also be proteins, such as granulocyte colony stimulating factor, programmed cell death-1, vascular endothelial growth factor and interleukins. Cell therapeutics can be delivered by microburs, such as bacteria and virus. Alternatively, the therapeutic agent may be any suitable agent, such as for example an SSRI, which may be, for example, fluoxetine or citalopram.

In another embodiment, the core and the nanoneedles each may optionally comprise a metal oxide, such as (without limitation) manganese oxide, zinc oxide, gold, silicon dioxide, or titanium oxide. The metal oxide may optionally be: doped with a functional agent, such as (without limitation) silver, iron, aluminum, or a transition metal, or with a surface conjugate, such as (without limitation) (3-aminopropyl) triethoxysilane (APTES); or coated with a functional agent, such as (without limitation) PEI, dextran, alginate, pullulan, hyaluronic acid, polyethylene glycol, a β-glucan, or chitosan.

Another embodiment uses a hollow core in the bio-microbur for carrying a therapeutic agent.

Another embodiment provides a method of delivering a therapeutic agent by administering to a patient the therapeutic agent with a bio-microbur therapeutic delivery platform using any of the bio-microburs as described above. The administration to the patient may optionally be oral administration. The bio-microbur therapeutic delivery platform and therapeutic agent may optionally be delivered orally to the patient in a capsule, and/or in a hydrogel format. Optionally, the therapeutic agent is an SSRI, such as fluoxetine or citalopram.

Further, optionally the SSRI is combined with the therapeutic delivery platform in a MB-MSN-SSRI configuration.

Alternatively, for example, the administration to the patient may be parenteral administration. Optionally, the parenteral administration of the bio-microbur therapeutic delivery platform may include at least one type of cell to which the delivery platform adheres.

Another embodiment provides a method of preparing a bio-microbur therapeutic delivery platform, comprising the steps of preparing the bio-microburs before combining them with the treating agent. Optionally, the preparation of the bio-microburs may include adding $Mn(CH_3COOH)_2 \cdot 4H_2O$ to $(NH_4)_2S_2O_8$ to form a first solution; adding sulfuric acid to the first solution to form a second solution; heating the second solution to form a precipitate of bio-microburs; and extracting and washing the bio-microburs. Alternatively, the preparation of the bio-microburs may include adding an aqueous solution of $Zn(CH_3COOH)_2 \cdot 2H_2O$ to an aqueous solution of NaOH to form a solution; heating the solution to form a precipitate of bio-microburs; and washing and drying the bio-microburs.

These and other features of the present subject matter will become readily apparent upon further review of the following specification.

BRIEF DESCRIPTION OF THE DRAWINGS

FIG. 11A compares the microbur size, in μm; FIG. 11B compares the Zeta potential of the microburs MB0.5, MB2, MB6, and MB12 in mV. FIG. 11C compares the average number of nanospikes per microbur, for MB 0.5, MB2, MB6, and MB12.

Similar reference characters denote corresponding features consistently throughout the attached drawings.

DETAILED DESCRIPTION OF THE PREFERRED EMBODIMENTS

The bio-microbur therapeutic delivery platform is a three-dimensional (3D)-oriented nanoneedle platform having a shape simulative of a microscale version of a fruit bur-typically a seed or dry fruit with hooks or teeth. The bio-microbur may be used for drug delivery and other biological applications. Similar to the ability of the fruit bur to adhere to many different types of surfaces (e.g., fur, ground and plants) with its hooks or teeth, the bio-microbur therapeutic delivery platform with a multitude of needs or spikes provides superior retention to biological tissue (e.g., pig intestines), cell membranes (e.g., macrophage membranes), and biological gels (e.g., alginate hydrogels), especially when compared to conventional delivery vehicles such as nanoparticles and microparticles.

The bio-microbur therapeutic delivery platform includes a core and a plurality of nanoneedles secured to a surface of the core and extending outwardly therefrom. The plurality of nanoneedles may be adapted for carrying and/or delivering a therapeutic agent. The core and the plurality of nanoneedles may be, for example, coated with the therapeutic agent, or may be comprised in whole or part of the therapeutic agent. Alternatively, or used in combination with the previous example, the core may be hollow for additional capacity in carrying the therapeutic agent. The bio-microbur therapeutic delivery platform and the therapeutic agent may be delivered to the patient through injection or oral delivery, and may be formed from a biodegradable material.

Figure 1:
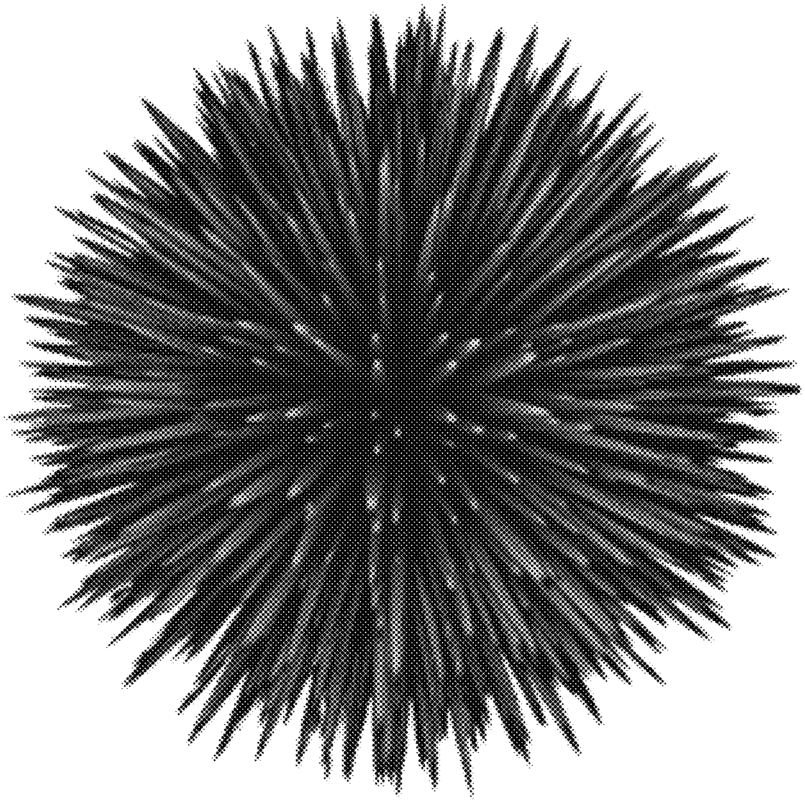
FIG. 1 shows a single example of a bio-microbur of the bio-microbur therapeutic delivery platform.
Figure 2:
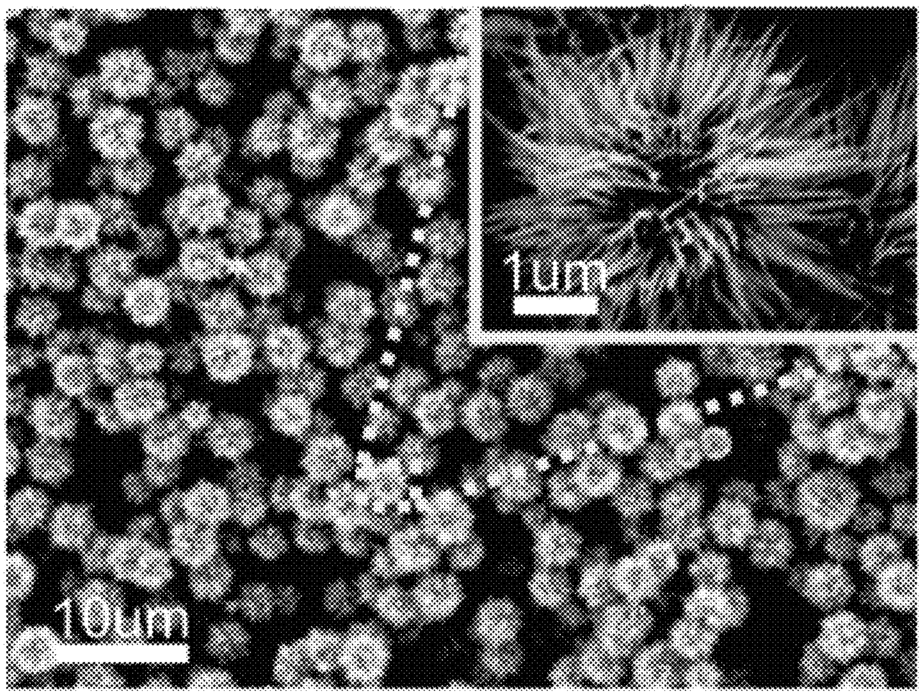
FIG. 2 is an electron microscope image of the bio-microbur therapeutic delivery platform, with an enlargement of a single microbur.
Figure 4A:
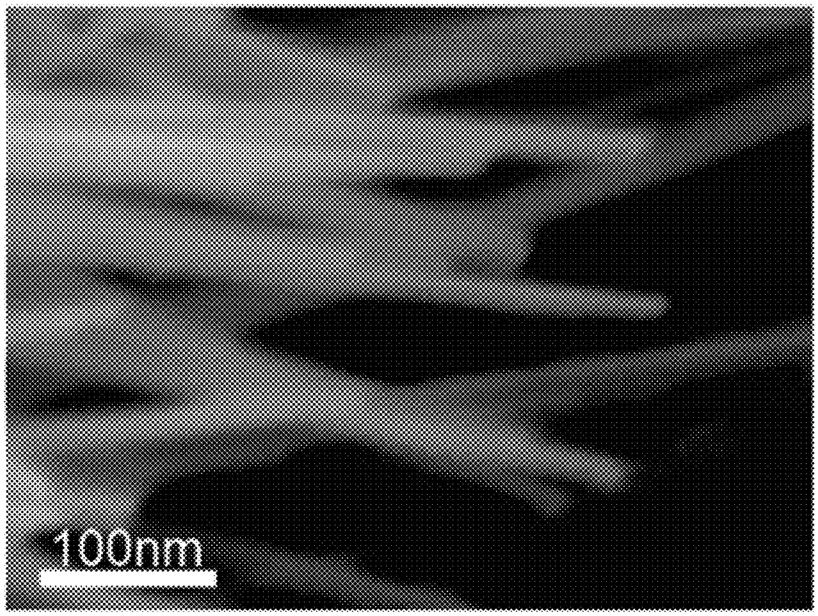
FIG. 4A is an electron microscope image of nanoneedles of a bio-microbur.

Although FIGS. 1, 2, and 10A to 10H show the bio-microbur having a spherically symmetric shape with a substantially spherical core, it should be understood that the core may have any suitable shape, such as, for example, a rod, a sheet or the like. Additionally, although FIG. 2 shows the bio-microbur at the μm scale, it should be understood that the nanoneedles may have any suitable length, including but not limited to tip of 1-10 nm, height of 0.5-2 μm, microbur of 1-3 μm, and coating of 2-20 nm. The overall bio-microbur may have a size, for example, of approximately 100 nm to approximately 100 μm, such as, for example, 1 to 3 μm. The density of nanoneedles on the surface may be in the range of 10 million per $cm^2$, to 100 per $cm^2$. FIG. 4A illustrates the three-dimensional (3D) orientation of the nanoneedles. It should be understood that the bio-microbur therapeutic delivery platform may be used to carry any suitable therapeutic agent. Non-limiting examples of such agents include small molecules, proteins, nucleic acids, sugars, lipids, and the like, such as for example, an SSRI, such as fluoxetine.

Figure 3A:
FIG. 3A illustrates the adherence of bio-microburs to tissues, biological membranes, and biological gels.
Figure 3B:
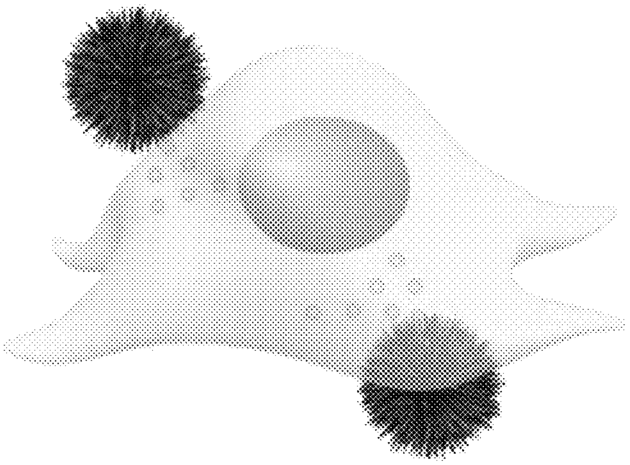
FIG. 3B illustrates the penetration of cell membranes by nanoneedles of the bio-microbur therapeutic delivery platform.
Figure 3C:
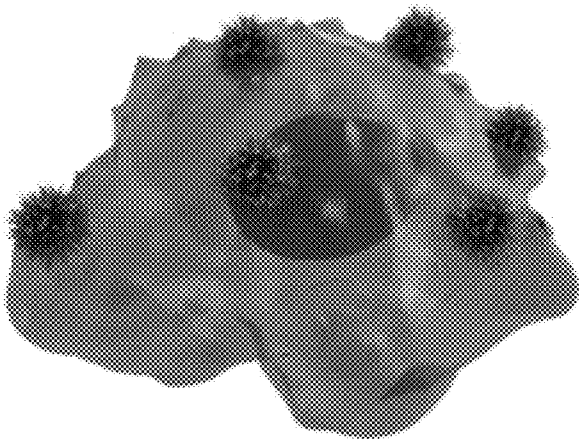
FIG. 3C illustrates nanotopographical manipulation of cell behavior with the bio-microbur therapeutic delivery platform.

The nanoneedles allow the bio-microbur to adhere to biological gels and cell membranes in a manner similar to that of the macroscale fruit bur. It should be understood that the nanoneedles may merely adhere to the biological gels and cell membranes or may at least partially penetrate them. For example, FIG. 3A illustrates the enhanced retention of the bio-microbur to tissues, biological membranes, and gels for regiospecific drug delivery, and FIG. 3B illustrates nanoneedle-mediated penetration of cell membranes. The nanoneedles also make possible other biological manipulations, such as, for example, regulating fluid and gel shearing topography. FIG. 3C illustrates such nanotopographical manipulation of cell behavior. The nanoneedles also greatly increase the overall surface area of the bio-microbur, thus providing additional surface area for drug loading and releasing.

Figure 4B:
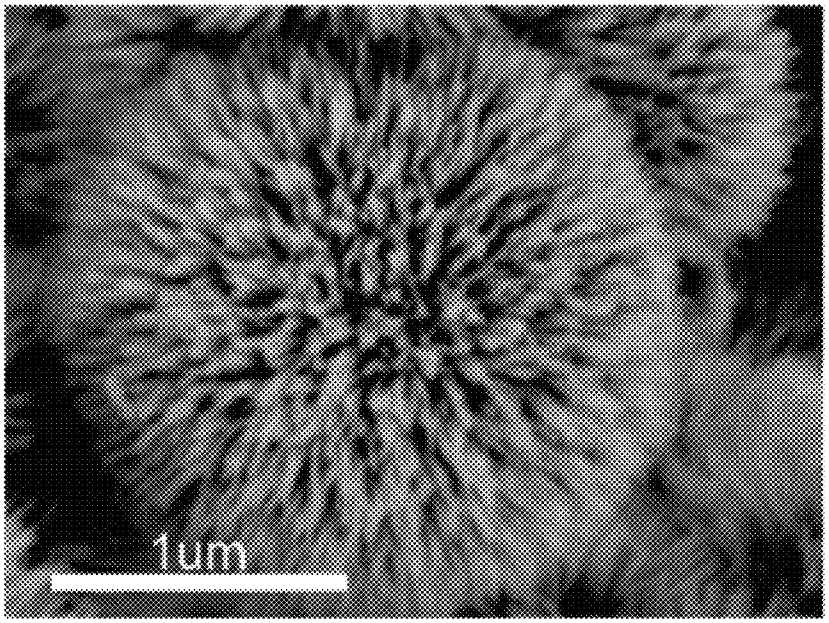
FIG. 4B is an electron microscope image of a bio-microbur therapeutic delivery platform formed from silver-doped manganese oxide.
Figure 4C:
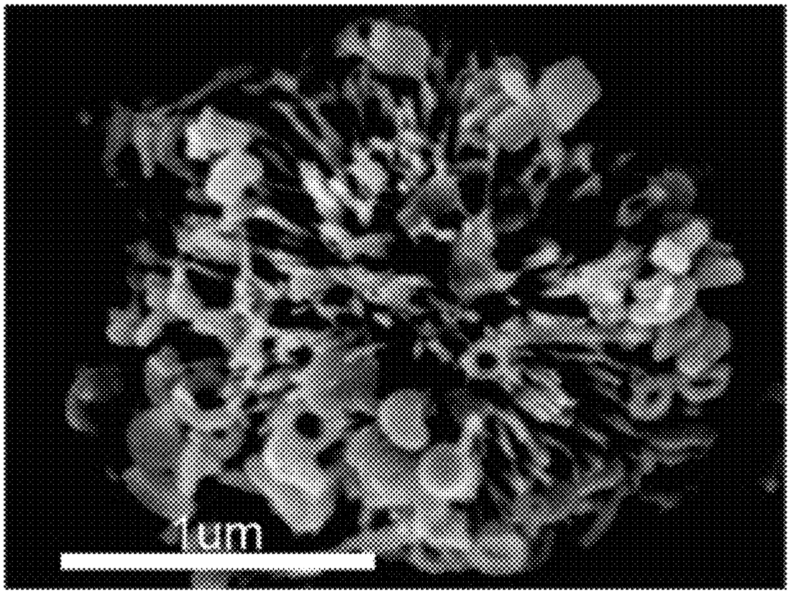
FIG. 4C is an electron microscope image of a nanoparticle-loaded bio-microbur.
Figure 4D:
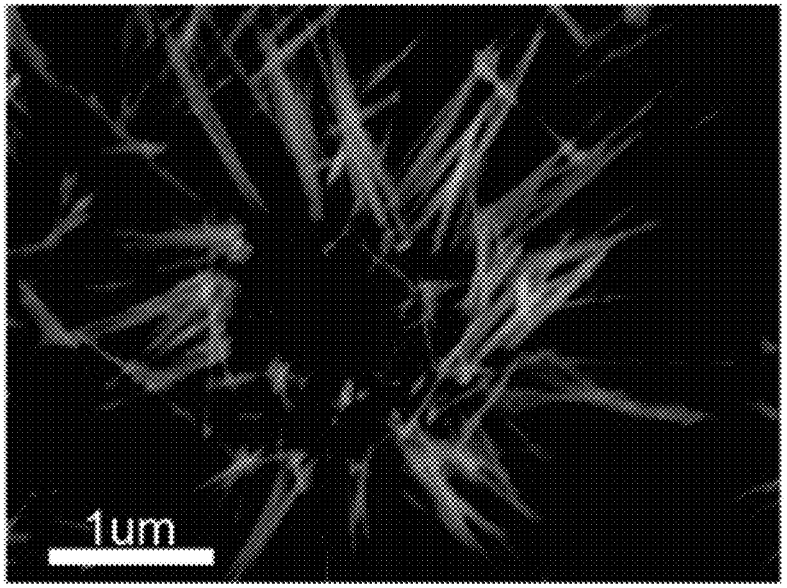
FIG. 4D is an electron microscope image of a bio-microbur with a hollow core.

The core and the plurality of nanoneedles may also each be formed from a metal oxide, such as, but not limited to, manganese oxide ($MnO_2$), zinc oxide (ZnO), gold, silicon dioxide ($SiO_2$) or titanium oxide ($TiO_2$). Additionally, the metal oxide may be doped with a functional agent, such as, but not limited to, silver, which has antimicrobial properties, iron, which may be used in imaging and the like, selenium, aluminum, or a transition metal. FIG. 4B shows a bio-microbur formed from silver-doped manganese oxide. FIG. 4C shows a nanoparticle-loaded bio-microbur, and FIG. 4D shows a bio-microbur with a hollow core for receiving the therapeutic agent.

As a further alternative, the metal oxide may be functionalized with a surface conjugate to assist in attaching the bio-microbur therapeutic delivery platform to a cell membrane, biological gel or the like. A non-limiting example of such a surface conjugate is (3-aminopropyl)triethoxysilane (APTES). As an additional alternative, the metal oxide may be coated with a functional agent to increase adhesion between the bio-microbur therapeutic delivery platform and a cell membrane, biological gel, or the like, such as, but not limited to, polyethyleneimine (PEI), dextran, alginate, pullulan, hyaluronic acid, polyethylene glycol, a β-glucan or chitosan.

In oral administration, the bio-microbur therapeutic delivery platform and the therapeutic agent may be delivered to the patient, for example, contained in a gelatin capsule, or integrated into a hydrogel or the like. The coating or container, such as a gelatin capsule, may be intended for example, to protect the microbur delivery agent from exposure to the high stomach pH, and to release the microburs once the formulation passes through the stomach to the intestines or other high pH environment-assuming that is the targeted area for delivery of the treating agent. When injected, for example, the bio-microbur therapeutic delivery platform may be delivered in a suitable liquid carrier prior to injection, for delivery to a targeted tissue or targeted cell membrane, such as that of a macrophage.

The superior and selective retention of the bio-microbur therapeutic delivery platform to targeted tissues and specific biological entities enables regiospecific drug delivery and has enormous potential as regiospecific treatment for any type of therapeutic treatment. The enhanced drug retention mediated bio-microbur may also directly enhance therapeutic efficacy. For example, nanoparticle-based oral gene delivery has shown enormous potential to treat a variety of diseases, but so far has suffered from a poor delivery efficiency. One of the critical barriers is the rapid clearance of nanoparticles in the gastrointestinal (GI) tract. The bio-microbur, however, strongly adheres to the mucin gels on surfaces of the GI, thus offering a promising solution to enhance the outcome of oral gene delivery. See, for example, FIG. 5.

The enhanced retention of the bio-microbur therapeutic delivery platform to the cell membrane has been experimentally validated and may lead to a variety of novel drug delivery applications. For example, immunotherapy based on the transplantation of immune cells, such as T cells and macrophages, represents a major medical breakthrough of the past decade. However, a lack of control over the fate of immune cells transplanted in vivo remains a major challenge.

Figure 5:
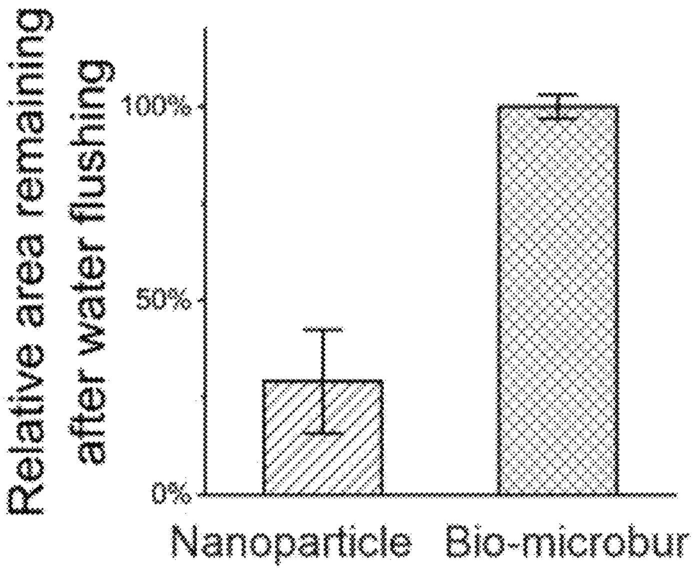
FIG. 5 is a graph comparing retention after water flushing of the bio-microbur therapeutic delivery platform to tissues, biological membranes and biological gels in comparison to a conventional nanoparticle carrier.

In recent experiments, the bio-microbur therapeutic delivery platform has exhibited a highly efficient (almost 100%) adherence to macrophages. Once the bio-microbur is loaded with immunomodulatory drugs, bio-microbur-bound macrophages can be injected into tumor sites with more predictive immunotherapy outcomes. FIG. 5 illustrates the enhanced retention of the bio-microbur, demonstrating relative area remaining after water flushing for the bio-microbur as compared to a conventional nanoparticle carrier.

Figure 6:
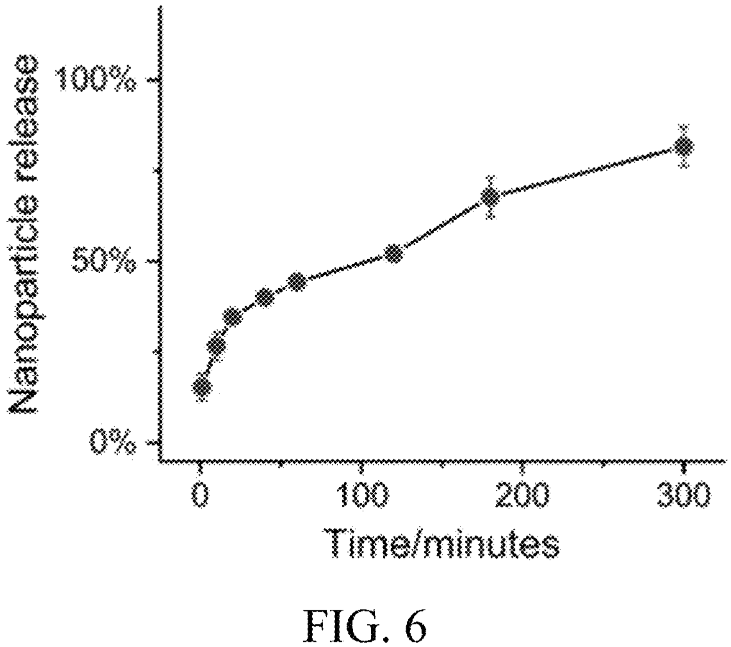
FIG. 6 is a graph showing sustained release of a therapeutic agent over time using the bio-microbur therapeutic delivery platform.

In addition to the materials discussed above, the bio-microbur may be at least partially formed from a dissolvable or biodegradable material and/or a dissolving time-release material, helping to provide sustained, controlled drug delivery, as reflected in FIG. 6.

The distinctive biomimetic, 3D-spiky-shaped bio-microbur can also be used in a wide variety of different biological applications. One unique advantage of the bio-microbur originates from its 3D-oriented, sharp nanoneedles formed on the surface, which forms the basis for a new means for gene therapy. For example, current approaches for gene delivery have been typically mediated by the endocytosis of cationic nanoparticle bearing nucleic acids, which often suffers from a limited efficiency to treat genetic diseases. However, the 3D-oriented nanoneedles of the bio-microbur, once loaded with nucleic acids or plasmids, may facilitate the penetration of the cell membrane and enable direct, rapid and efficient delivery of genes into cytosols. Although cytosol delivery of genes has been suggested using nano/micro-needle patches, such patches are much, much larger in scale, and therefore cannot be injected, instead often requiring invasive surgical procedures for application to internal organs.

Another advantage of the bio-microbur delivery platform is its tunable surface nanotopography for direct manipulation of cellular behaviors, which can be synergized with drug delivery for immunotherapy as well as other therapeutic applications. For example, polarization of macrophages critically determine their outcome in treating cancer and other diseases. Arrays of sharp nanoneedles have been previously used to transiently direct the polarization of macrophages to a pro-inflammatory state, which is desired for cancer immunotherapy. However, such arrays of nanoneedles, once seeded with macrophages, again cannot be easily injected by syringe, thus limiting their clinical potential.

In contrast, bio-microburs that strongly adhere to the macrophage cell membrane, impose nanotopography-mediated stimulatory effects, and that can simultaneously release proinflammatory drugs provide an excellent enhancer for macrophage-based immunotherapy. Other advantages originate from its unique biomimicry shape, including, but not limited to, high surface area (and/or cavity) for drug loading and release, tunable biodegradability and high biocompatibility, the existence of metal species for scavenging cytotoxic and immunogenic cell-free nucleic acid and reactive oxygen species, and unconventional fluid shearing during blood circulation. Taken together, the bio-microbur therapeutic delivery platform presents enormous advantages for a broad range of biological applications, including drug delivery including oral delivery of biologics such as nucleic acids, proteins, lipids and polysaccharides, which may be used for vaccines, gene therapy, immunotherapy, and many others.

Figure 8:
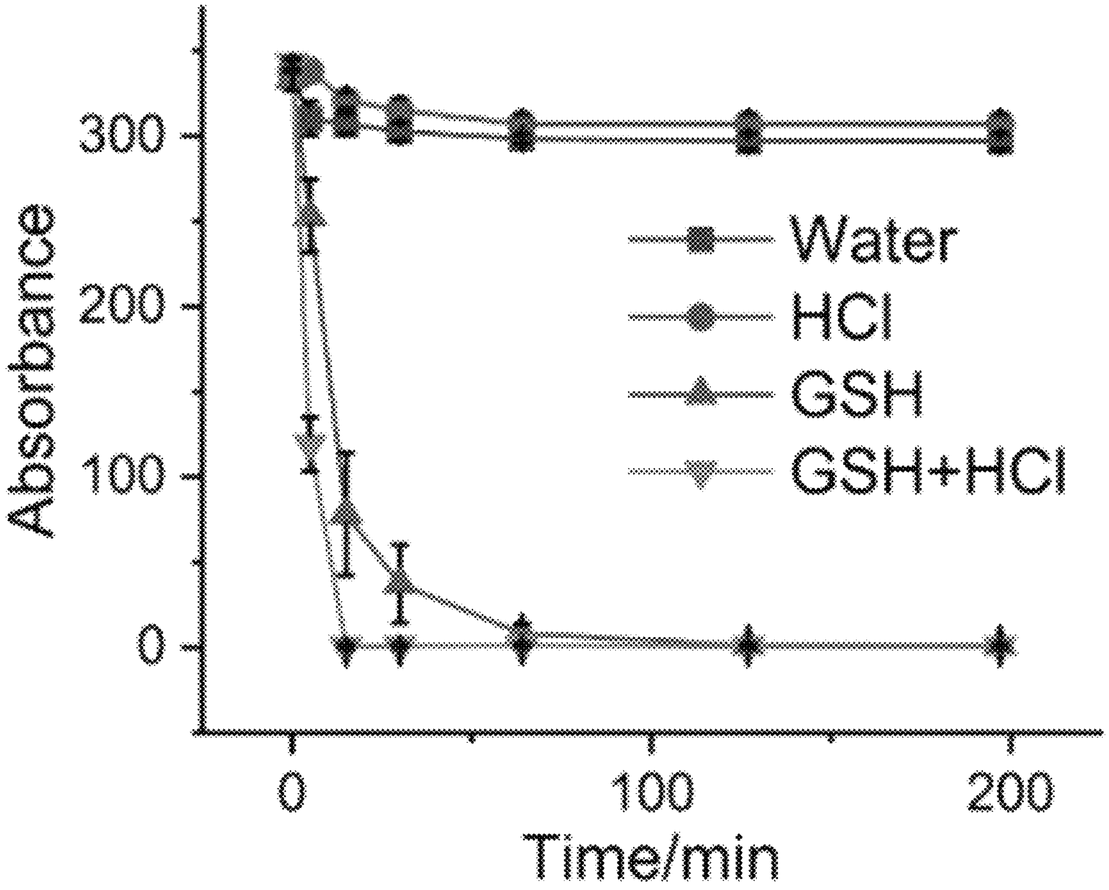
FIG. 8 is a graph showing the controlled degradation of the bio-microbur therapeutic delivery platform.

The bio-microbur therapeutic platform may be tuned in its synthesis to precisely control the composition, structure, surface, and flexibility in order to incorporate different therapeutic molecules for the treatment of a variety of diseases. The bio-microbur therapeutic platform may be used to treat cells and cell organelles, destroy tissue debris, target specific types of cells, and may be used for either intracellular or extracellular (in vitro) treatment, as well as being used as a reactive oxygen species (ROS) scavenger and a scavenger for cell-free DNA. Additional non-limiting examples of types of treatments include intratumoral, intranasal, intravenous, blood vessel interaction, pulmonary (i.e., inhalation), microparticle depot, intracellular, and for live-cell therapies. Additionally, the bio-microbur therapeutic platform may be used to deliver cell mechano-transduction machinery and for immunocyte-targeted delivery. As shown in FIG. 8, the bio-microbur may also be tuned for a desired controlled biodegradation.

Figure 7A:
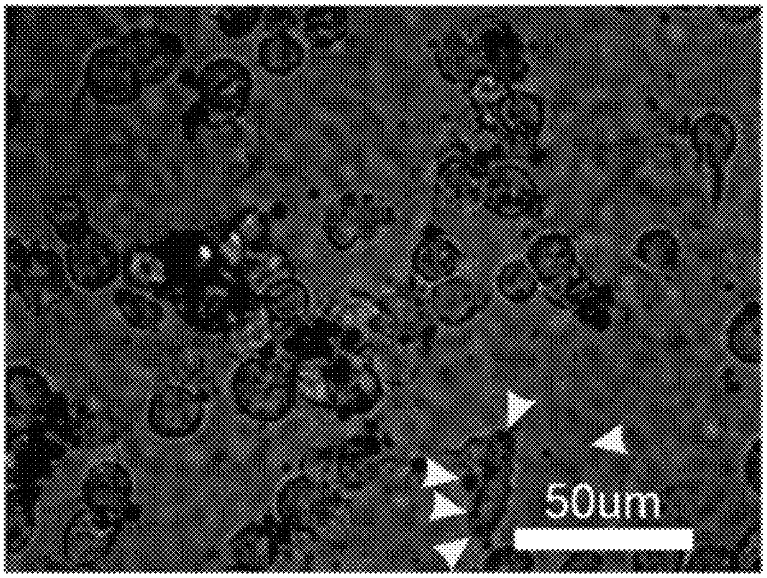
FIG. 7A and FIG. 7B are electron microscope images of the bio-microbur therapeutic delivery platform adhering to the cell membrane of a macrophage.
Figure 7B:
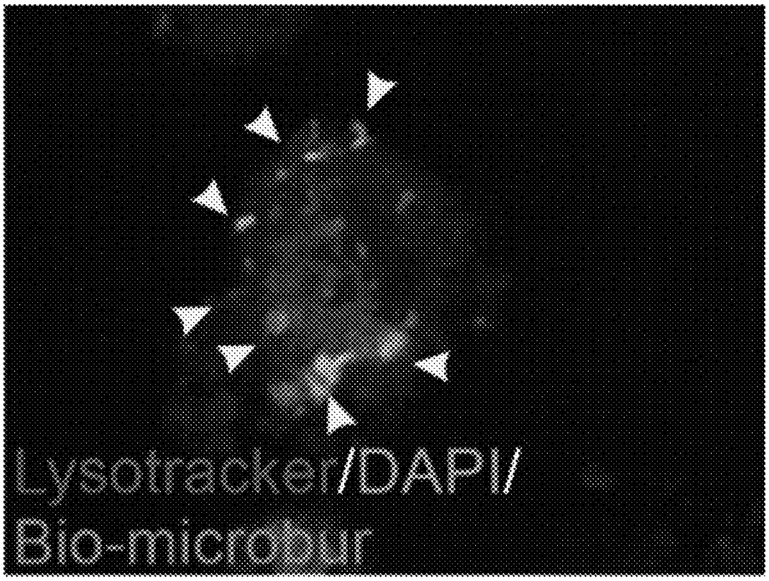
Figure 9A:
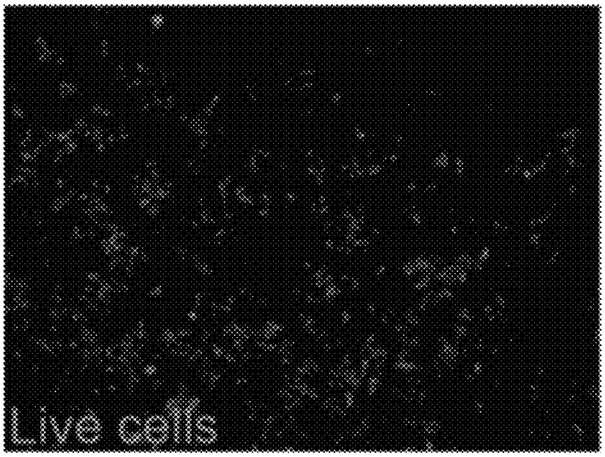
FIG. 9A, FIG. 9B and FIG. 9C are microscope images illustrating the biocompatibility of the bio-microbur therapeutic delivery platform.
Figure 9B:
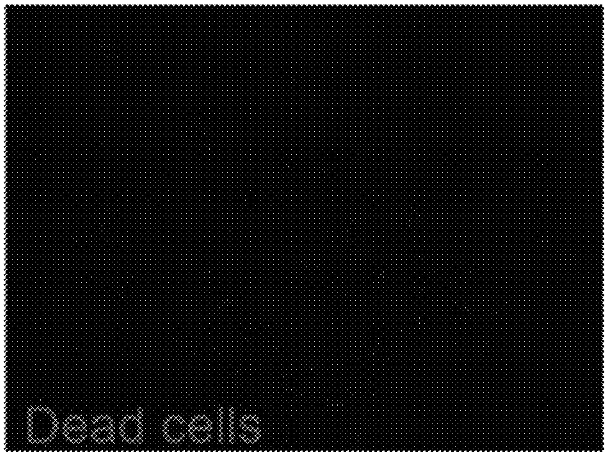
Figure 9C:
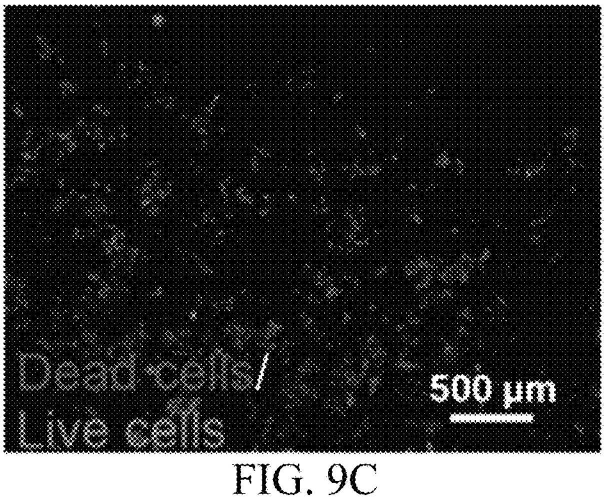

Depending on the type of treatment, the bio-microbur therapeutic delivery platform may be delivered to a wide variety of body systems or organs, such as, for example, the brain, the lungs, the skin, the liver, etc. As noted above, when administered to the patient, the bio-microbur therapeutic delivery platform may also be already attached to a cell, such as, for example, lymphocytes, T cells, B cells, NK cells, neutrophils and macrophages. FIGS. 7A and 7B show the bio-microbur adhering to macrophage cell membranes. The bio-microbur therapeutic delivery platform may be used to treat a wide variety of diseases and conditions, such as, but not limited to, breast cancer, brain cancer, skin cancer, prostate cancer, wound treatment, treatment of infectious diseases, such as cholera and the like, treatment of neurological disorders, dysfunctions in the liver, brain, skin, etc., treatment of oxidative stress-related diseases and the like. FIGS. 9A, 9B and 9C show the excellent biocompatibility of the bio-microbur (shown here at high concentrations of 500 μg/mL).

For each type of bio-microbur, a scanning electron microscope (SEM), a transmission electron microscope (TEM), and an optical microscope were used to confirm the morphology, structure, composition, and adhesive properties. HCT-116 colon cells, THP-1 monocyte-derived macrophages, Caco2 cells, and HT-29 large intestine cells were used to characterize the biocompatibility, gene transfection capacity, immune-stimulatory ability, and other biological properties of the bio-microburs. The biological properties were quantified by CCK-8 assay, live-dead assay, quantitative real-time polymerase chain reaction (qRT-PCR), and immunostaining. Pork intestine, chicken skin, alginate hydrogels, THP-1-derived macrophages, and HCT-116 colon cells were used for evaluating the adhesiveness of the bio-microburs on the biological membranes and surfaces by quantifying the remaining bio-microbur area after undergoing shearing stress from the fluid. Drug and gene delivery performance of each type of bio-microbur was tested using small molecules (e.g., rhodamine 6G, fluorescein), biologics (e.g., bovine serum albumin, nucleic acids, and lipids), and nanoparticles (e.g., plasmid-loaded chitosan-polyethyleneimine nanoparticles) by quantifying time-dependent release from bio-microburs.

Certain treating agents may benefit from specifically targeting certain parts of the body for delivery, such as, for non-limiting example, the gut epithelium. SSRIs may prove effective while avoiding side effects when delivered to the gut epithelium (the intestinal mucosa) using an appropriate form of microburs that may be delivered orally. The microbur technology provides distinct advantages compared to other technologies developed for delivery of treating agents to the intestinal epithelium.

(1) Drugs not absorbed by the gut epithelium are eradicated quickly through the GI tract by gut contractions. The 3D vertical nanoneedle-decorated design of this technology, however, enables the device itself to stay within the gut epithelium despite contractions, while continuing to release the treating agent.

(2) By comparison, microneedle-based drug delivery platforms that enhance GI adhesion typically but have larger microneedles that damage GI epithelium, which promotes translocation—and thus systemic absorption—of the treating agent. Such systemic absorption is avoided by the present microbur structures.

(3) Nanoneedle-based transdermic delivery patches cannot be adapted for oral delivery.

In contrast, the present biocompatible, 3D vertical nanoneedle-decorated microparticle-based delivery platform addresses these key issues, and thus more easily facilitates the safe, reliable, convenient, and targeted oral delivery of SSRIs to the gut epithelium.

Example 1

To prepare bio-microburs with a composition of doped or un-doped $MnO_2$, in 50 mL plastic centrifuge tubes, aqueous solutions of $Mn(CH_3COOH)_2 \cdot 4H_2O$ were first prepared at a concentration of 3.65 g per 200 mL and $(NH_4)_2S_2O_8$ at a concentration of 3.90 g per 200 mL, which was enough for 10 reactions (40 mL total volume for each reaction). 20 mL of the $Mn(CH_3COOH)_2 \cdot 4H_2O$ aqueous solution was added to 20 mL of $(NH_4)_2S_2O_8$ drop by drop under vigorous stirring at 1200 rpm for 10-20 minutes until the solution became pale yellow. 1.6 mL of concentrated sulfuric acid ($H_2SO_4$, 95-98%) was added to the yellow solution. The solution continued to stir for 10 minutes. The solution was transferred to a 40 mL hydrothermal chamber and heated from room temperature to 120° C. within 30 minutes, followed by continuous heating at 120° C. for 5 hours. The $MnO_2$ bio-microburs (black-colored precipitates) were washed with water and ethanol two times each, until the pH became neutral (pH=7). The bio-microburs were washed using freeze-drying instruments. To dope the bio-microburs with different amounts of silver, aluminum, iron, and other ions, the nitrate salts with varying amounts were added in the first step, together with the $Mn(CH_3COOH)_2 \cdot 4H_2O$. To modulate the size, shape, and structure of the bio-microburs, concentrations of the precursors in the first step, and the temperature and heating times were varied.

Example 2

In order to make ZnO bio-microburs, solutions of NaOH (0.64 g/4.0 mL-DIW), along with a $Zn(CH_3COOH)_2 \cdot 2H_2O$ solution (0.36 g/4.0 mL-DIW) (enough for 10 reactions (40 mL solution each)) were first prepared. At room temperature, the $Zn(CH_3COOH)_2 \cdot 2H_2O$ solution was added to the NaOH solution (0.64 g/4.0 mL-DIW) drop by drop under vigorous stirring for 10-60 minutes until the solution became clear. 8.0 mL of the clear, mixed solution was transferred to a 10 mL glass vial. The vial was then capped and sealed with parafilm. The vial containing the mixed solution was heated at 40° C. for 1, 2, 4, 8, 12, 24, and 48 hours. After ~5 min, the solution became turbid. After 1 hour, the ZnO bio-microbur shape began to form. Longer times resulted in longer nanoneedles. The bio-microburs in each vial were washed three times using deionized water (DIW) under centrifuge (3000 rpm, 5 minutes), then the bio-microburs were dried in a 90° C. overnight.

Example 3

To coat the bio-microburs of Example 1 or Example 2 with a biopolymer (e.g., a chitosan coating), chitosan was prepared as a stock solution. For example, 100 mL 1% acetic acid DIW solution was prepared in a 500 mL beaker, and 5 g of chitosan powder was added into the acetic acid DIW solution. A magnetic stirring bar was added, and the mixture was stirred vigorously. The mixture became very viscous and sticky, so the stirring speed was adjusted accordingly. Stirring occurred for 12-36 hours, and the solution became gel-like. The gel-like solution was transferred into 50 mL centrifuge tubes and stored properly. There was less than 50 mL of solution that could be transferred from the original 100 mL solution. 1-2 mL gel-like chitosan solution was transferred by directly pouring it into a 50 mL clean beaker with a stirring bar inside. The amount of chitosan solution was estimated based on the weight of the beaker, before and after the transfer. 5-10 mL of water was added into the beaker to make a 1-10 mg/mL chitosan solution by stirring. 1-50 mg of bio-microbur powder, for example using the ZnO bio-microburs mentioned above, was placed in a 50 mL centrifuge tube, DIW (10-20 mL) was added, and this was followed by vigorously shaking/vortexing to break the powder into individual microparticles and form a bio-microbur suspension. The bio-microbur suspension, for example a ZnO bio-microbur suspension, was slowly added (shaking the suspension each time before adding) into 5 mL of the 10 mg/mL chitosan solution with vigorous stirring. The reaction took approximately 12 hours, then 1-10 mL 1× or 10×PBS was added slowly, and the reaction was continued for another 12 hours. When 10 mg/mL chitosan solution was used, the solution became cloudy due to the precipitation of chitosan. Washing with DIW was performed by centrifugation or gravity precipitation, keeping the aggregates in the bottom of centrifuge tubes. Washing was repeated 3-6 times, and the bio-microburs were maintained in DIW or buffer conditions (being careful to not let it dry).

Example 4

Figure 10A:
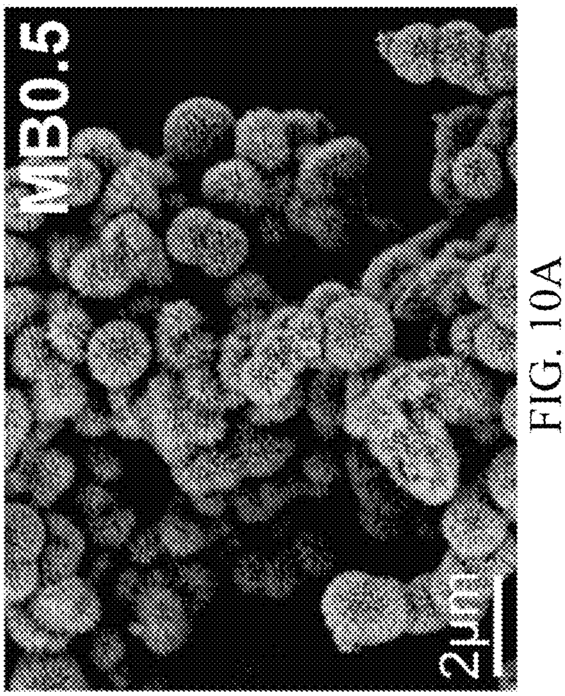
FIG. 10A, FIG. 10C, FIG. 10E, and FIG. 10G are electron microscope images, at 2 μm magnification, of the bio-microbur produced from a reaction duration of 0.5 hours, 2 hours, 6 hours, and 12 hours, respectively.
Figure 10B:
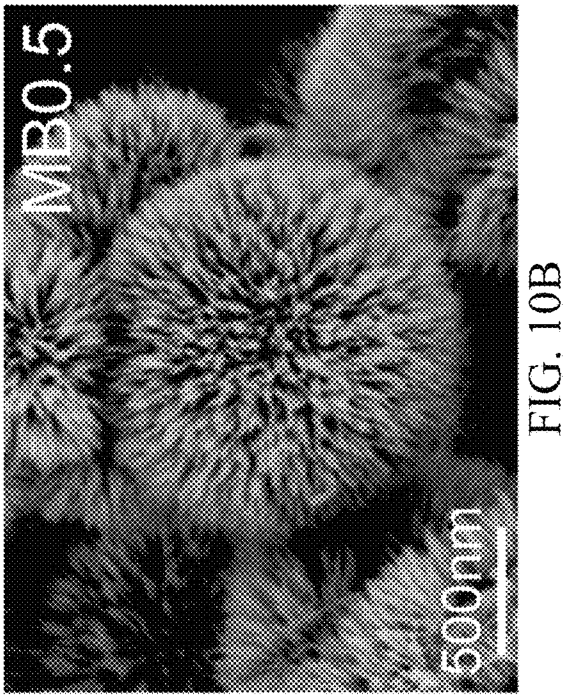
FIG. 10B, FIG. 10D, FIG. 10F, and FIG. 10H are electron microscope images of the same microburs produced from the reaction duration of 0.5 hours, 2 hours, 6 hours, and 12 hours, respectively, shown at a different magnification.
Figure 10C:
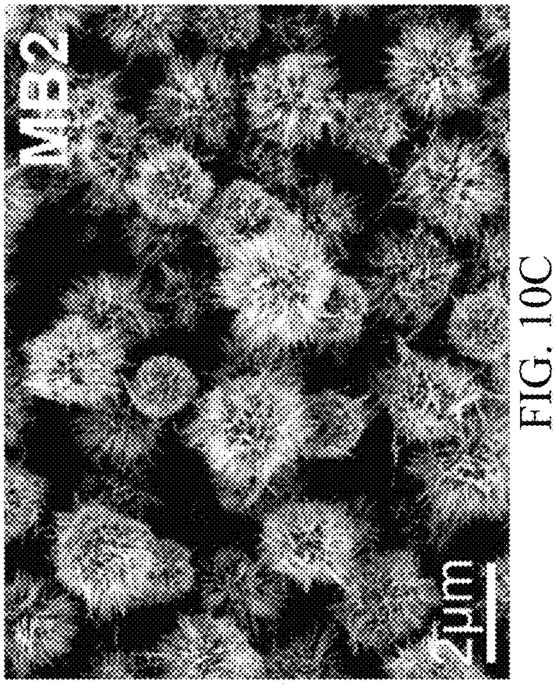
Figure 10D:
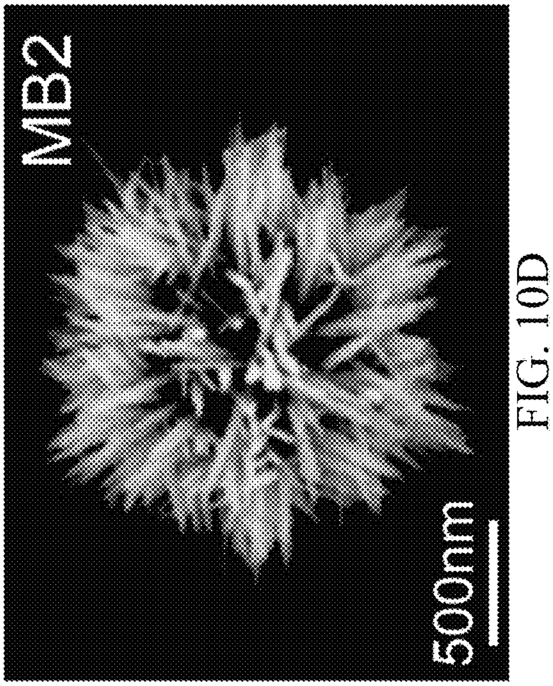
Figure 10E:
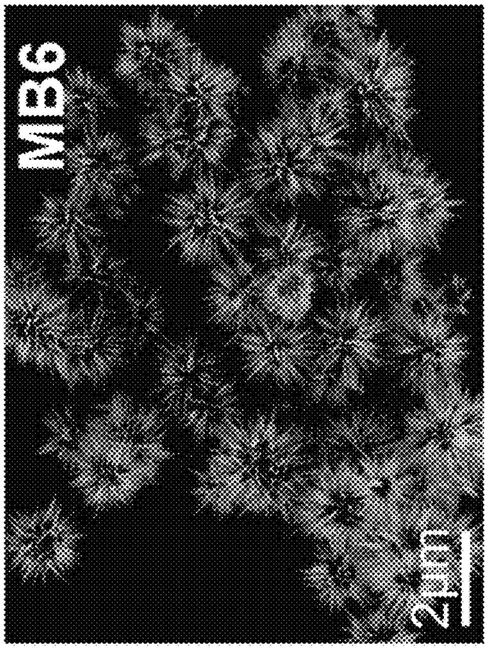
Figure 10F:
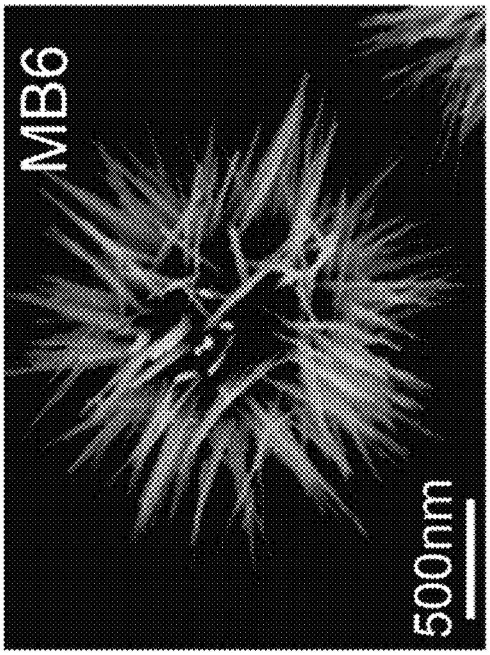
Figure 10G:
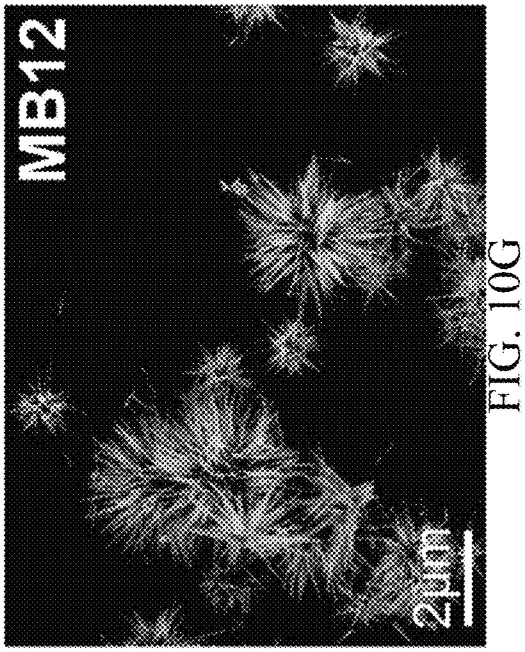
Figure 10H:
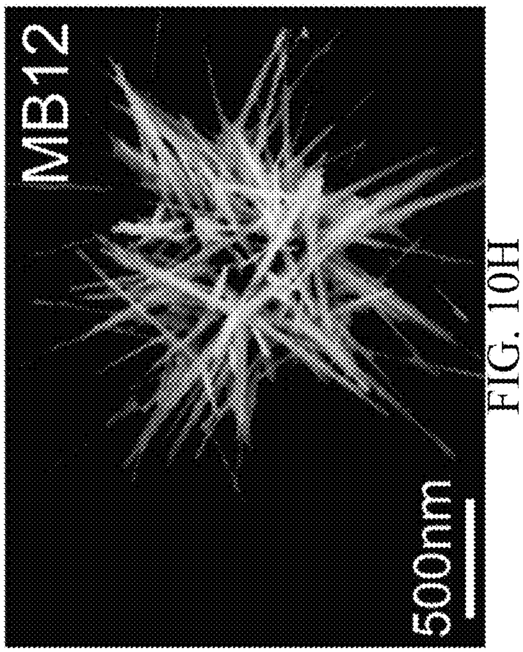

Modifying the reaction time can change the size and configuration of the microbur, including their Zeta potential, and the number of spikes per microbur. In a typical synthesis, manganese dioxide microburs were generated from a redox reaction between manganese (II) salt and ammonium persulfate. We compared reaction times of 0.5 hours, 2 hours, 6 hours, and 12 hours. FIGS. 10A through 10H are electron microscope images of the structures of the microburs after 0.5 hours (MB0.5), 2 hours (MB2), 6 hours (MB6), and 12 hours (MB12), at 2 μm and at 500 nm magnification. FIG. 10A and FIG. 10B show the MB0.5 microburs; FIG. 10C and FIG. 10D show the MB2 microburs; FIG. 10E and FIG. 10F show the MB6 microburs; and FIG. 10G and FIG. 10H show the MB12 microburs.

Figure 11A:
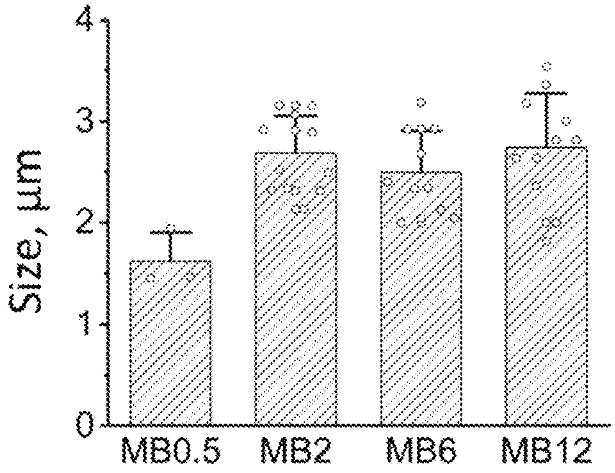
FIG. 11A, FIG. 11B, and FIG. 11C compare the microburs produced after reaction duration of 0.5 hours (MB0.5), 2 hours (MB2), 6 hours (MB6), and 12 hours (MB12).
Figure 11B:
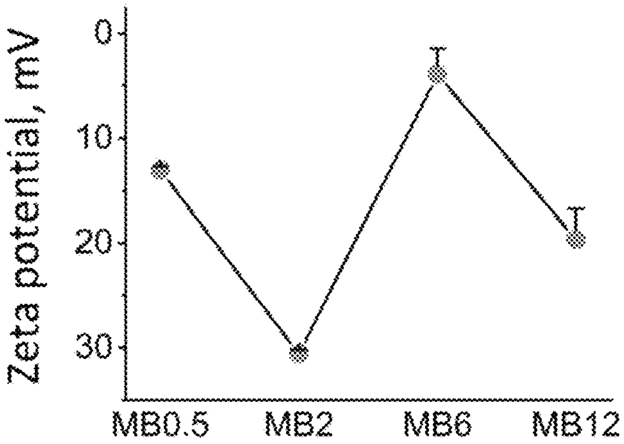
Figure 11C:
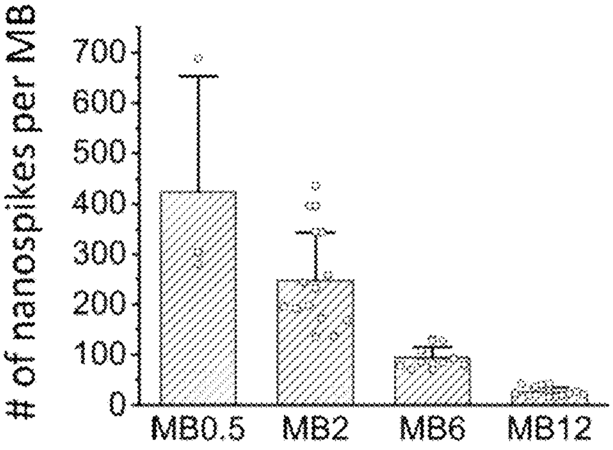

FIG. 11A is a graph of the difference in size of the resulting microburs with the 0.5-hour reaction time resulting in the smallest microburs (about 1.6 μm, MB0.5) while 2-, 6-, and 12-hour reaction times resulted in microbur sizes of about 2.5 to over 3 μm (MB2, MB6, and MB12, respectively). FIG. 11B shows the differences in Zeta potential, measured in mV, for MB0.5, MB2, MB6, and MB12, ranging from about 30 mV for MB2 to about 4 mV for MB6. FIG. 11C shows the difference in number of nanospikes per microbur, ranging from about 25 for MB12 to over 400 for MB0.5.

Example 5

Figure 12:
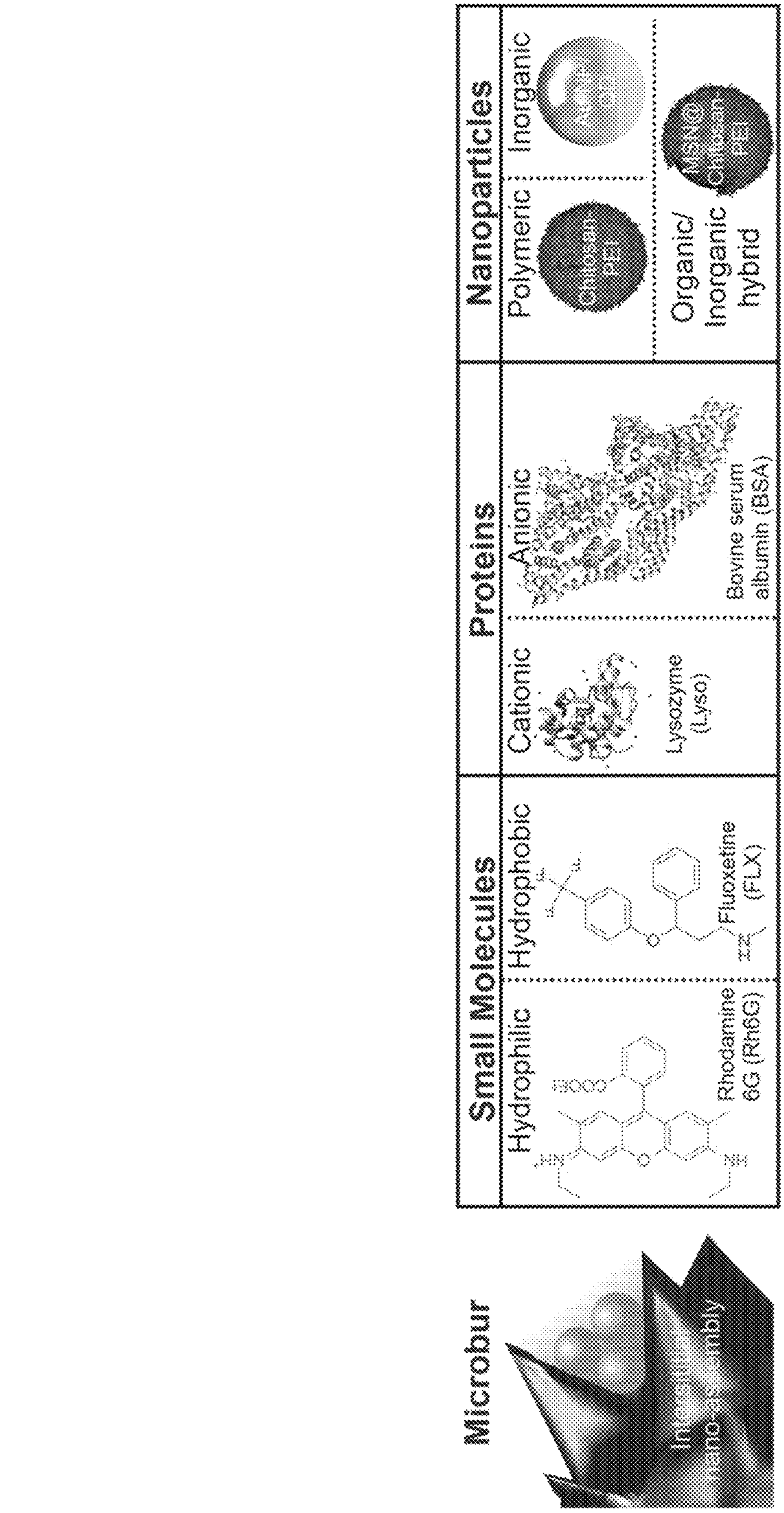
FIG. 12 depicts a microbur with interstitial nano-assembly of microbur with loaded drug, with examples of drugs that comprise hydrophilic or hydrophobic small molecules, cationic or anionic proteins, and polymeric, inorganic, or hybrid nanoparticles.

The microburs may be used to deliver a wide variety of treating agents. FIG. 12 depicts an interstitial nano-assembly for drug loaded microburs and lists a number of general and specific examples of treating agents. For example, the treating agent may be in the form of a small molecule, such as a hydrophilic agent (such as Rhodamine 6G) or a hydrophobic agent (such as Fluoxetine); a protein, which can be cationic (such as lysozyme) or anionic (such as bovine serum albumin); or a nanoparticle, such as a polymeric agent (such as chitosan-PEI), inorganic agent (such as Au NP/QD), or an organic/inorganic hybrid (such as chitosan polyethyleneimine coated mesoporous silica).

Example 6

Targeting SSRIs to the gut epithelium provides a novel way to achieve effective treating using the SSRIs while eliminating side effects. The microbur formulation allows for oral delivery while targeting release of the treating agent to the intestinal mucosa.

Figure 13A:
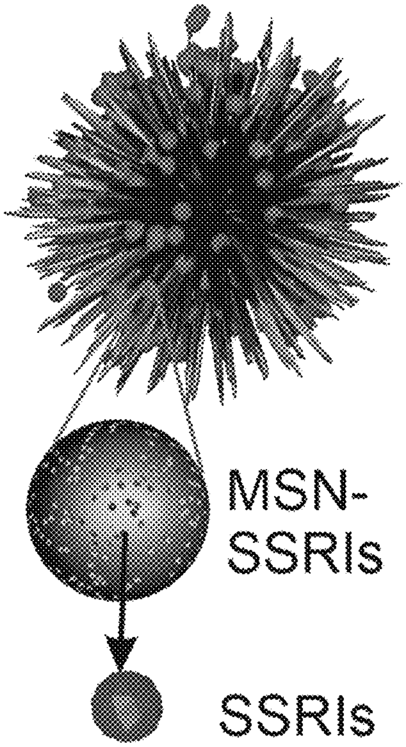
FIG. 13A depicts a magnified microbur-MSN-SSRI configuration, with SSRI loaded on the MSN-SSRIs which are then loaded on the microbur.
Figure 13B:
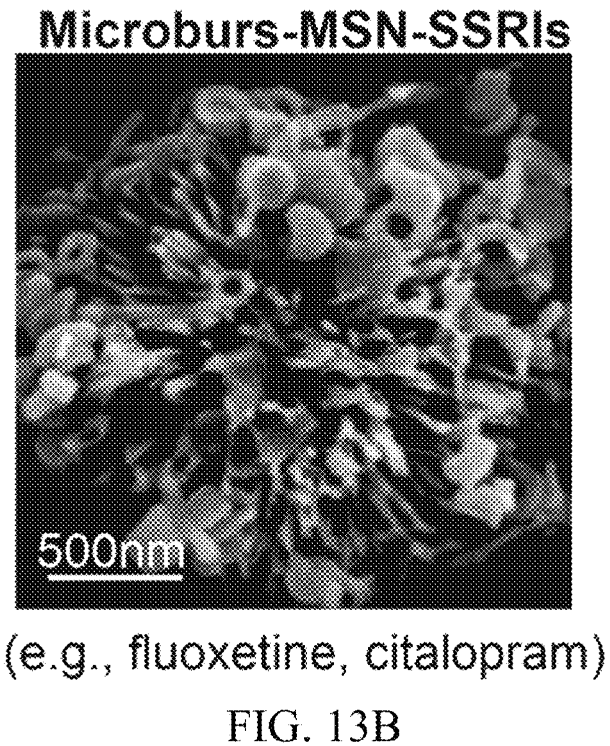
FIG. 13B is an electron microscope image of a microbur-MSN-SSRI configuration.

For oral delivery of SSRIs, such as fluoxetine or citalopram, we constructed a microbur-MSN-SSRI configuration combining microburs, mesoporous silica nanoparticles (MSNs), and the SSRI agent. FIG. 13A depicts the structure of the MB-MSN-SSRI configuration, while FIG. 13B is an electron microscope image of the MB-MSN-SSRIs. The microburs were synthesized from a redox reaction between manganese (II) ions and ammonium persulfate under high temperature (in a range from 80 to 180 Celsius degrees) and pressure (in a range from 2 to 20 atmosphere pressure).

Figure 13C:
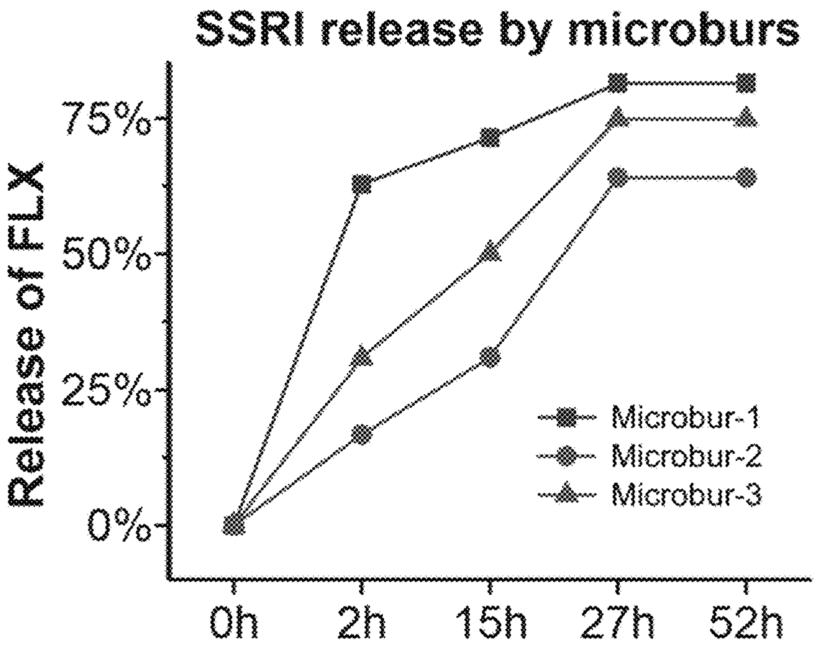
FIG. 13C is a chart comparing the release of SSRI (fluoxetine) through 52 hours after administration, where the microburs were produced by synthesis times of 2 hours (Microbur-1), 6 hours (Micobur-2), or 12 hours (Microbur-3).

We developed a microbur-based nanoparticle loading and dispersion system (MB-MSN-SSRIs) for epithelial-restricted targeting of SSRIs. We utilized a hollow manganese (Mn) dioxide MB loaded with SSRI encapsulated mesoporous silica nanoparticles (MSN-SSRIs; see FIGS. 13A to 13C). All components have known biocompatibility. The MB sizes range from 1-5 μm, and do not penetrate the mucosal layer yet robustly adhere to it. This significantly enhances their retention in the GI tract without causing translocation through the intestinal epithelium. The microburs are also highly stable in acidic conditions, allowing it to bypass the stomach.

These microbur structures efficiently (>50% of total weight) and rapidly (<5 minutes) adhere to the mucus of the intestine, where they degrade in the mucus rich glutathione (~1 mM) thereby initiating the release of the MSN-SSRIs into the mucosal layer of the intestine in a controllable manner (hours to days). The system thus provides targeted delivery and efficacy of the SSRI treating agent with minimal diffusion across the epithelial barrier, providing decreased systemic distribution of the treating agent.

In addition to the preventing translocation across the intestinal epithelial barrier, there are further advantages to this system that prevent systemic absorption: (1) the release of Mn ions, associated with the MB degradation, activates Ca2+-dependent adhesion molecules (cadherin), and/or directly upregulates expression of tight junction-related genes (e.g., claudin, occludin), thereby enhancing the integrity of epithelial tight junctions. As such, the degradation product may further reduce SSRI diffusion across the intestine, and into the bloodstream, by enhancing the integrity of gut epithelial tight junctions. (2) The tunable sizes and internal pore diameters of MSNs provide a secondary barrier to restrict drug diffusion. To further enhance targeted delivery into the intestinal epithelium, nanoparticles encapsulating SSRIs can be functionalized with epithelial-targeting ligands loaded to the microscale device. Further, drug release can be targeted to the different parts of the GI tract based on MB modifications.

Example 7

We prepare a microbur-based nanoparticle loading and dispersion system for epithelial-restricted targeting of SSRIs. We use a hollow manganese dioxide microbur loaded with SSRI-encapsulated chitosan-polyethyleneimine-polyboronic acid (chitosan-PEI-PBA) nanoparticles. The microbur has sizes ranging from 1-5 μm that do not penetrate the mucosal layer yet robustly adhere to it, a feature that significantly enhances their retention in the GI tract while avoiding substantial systemic delivery of the treating agent.

This microbur is also highly stable in acidic conditions, allowing it to bypass the stomach when delivered orally. In contrast, the microburs rapidly degrade in the mucus-rich glutathione (~1 mM) of the intestine, thereby initiating release of the chitosan-PEI-PBA nanoparticles encapsulated with SSRIs within several hours-roughly one cycle of intestinal mucus turnover. After adhesion to the mucus, the microscale devices release SSRIs into the mucosal layer of the intestine and stay within the epithelium, allowing targeted SSRI delivery to the mucosa without diffusion across the epithelial barrier.

The microscale delivery devices are small enough to be dispersed in common biological buffers (e.g., saline), gels (e.g., gelatin gels), or tablets, and are easily administrated orally. The microscale devices also efficiently (e.g., >10% of total weight) adhere to the mucus of the intestine, colon, or any other parts of the GI tract, and can be directed to a particular part of the GI tract based on pH levels.

To further enhance the targeted delivery into the intestinal epithelium, nanoparticles encapsulating SSRIs may be functionalized with epithelial-targeting ligands loaded to the microscale device.

Example 7

The release rate of treating agent may be tuned by modulating the microbur structure. For example, the release rate of orally delivered SSRIs, such as fluoxetine (FLX), in a MB-MSN-SSRI configuration could be tuned by modifying the reaction time used to produce the microburs with desired properties, to release the SSRI to intestinal epithelial cells by affixation to the mucosal lining. See FIG. 13C. Locally deposited SSRI helps minimize systemic absorption into the blood, CNS (central nervous system), or ENS (enteric nervous system).

Microburs are synthesized from a redox reaction between manganese (II) ions and ammonium persulfate under high temperature and pressure. Modifying the reaction time affects the microbur structure. Prolonged reaction time from 2 hours (Microbur-1) to 6 hours (Microbur-2) is typically associated with reduction of spikes, enlargement of hollow cores, and may thus increase surface area for drug binding and sustainable release. Prolonged reaction from 6 hours to 12 hours (Microbur-3), however, would result in disruption of the hollow core structures and leading to burst release. Microburs synthesized from 2 hours, 6 hours, to 12 hours reaction time are denoted in FIG. 13C as Microbur-1, Microbur-2, and Microbur-3, respectively, showing the release of FLX over 52 hours in pH 7.4 buffered solution. Microbur-2 shows the most-sustainable release of SSRIs. This comparison serves as an example of potential modulation of drug release through tuning the microbur structure by chemistry during construction of the microburs.

It is to be understood that the bio-microbur therapeutic delivery platform is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A bio-microbur therapeutic delivery platform, comprising:

a core having a surface; and a plurality of nanoneedles secured to the surface of the core and extending outwardly therefrom, wherein the plurality of nanoneedles are adapted for carrying and delivering a therapeutic agent, wherein the therapeutic agent is a selective serotonin reuptake inhibitor (SSRI), and wherein the bio-microbur therapeutic delivery platform and SSRI are combined in a microbur-mesoporous silica nanoparticle-SSRI (MB-MSN-SSRI) configuration.

2. The bio-microbur therapeutic delivery platform as recited in claim 1, wherein the core and the plurality of nanoneedles each comprise a metal oxide.

3. The bio-microbur therapeutic delivery platform as recited in claim 2, wherein the metal oxide is doped with a functional agent.

4. The bio-microbur therapeutic delivery platform as recited in claim 2, wherein the metal oxide is functionalized with a surface conjugate.

5. The bio-microbur therapeutic delivery platform as recited in claim 2, wherein the metal oxide is coated with a functional agent.

6. The bio-microbur therapeutic delivery platform as recited in claim 1, wherein the core is hollow for carrying the therapeutic agent.

7. The bio-microbur therapeutic delivery platform as recited in claim 1, wherein the plurality of nanoneedles are coated with the therapeutic agent.

8. The bio-microbur therapeutic delivery platform as recited in claim 1, wherein the core and the plurality of nanoneedles each comprise a biodegradable material.

9. The bio-microbur therapeutic delivery platform as recited in claim 8, wherein the core is spherical, and the nanoneedles have an average length of about 10 nm to 10,000 nm.

10. The bio-microbur therapeutic delivery platform as recited in claim 1, wherein the therapeutic agent is an oral vaccine or another oral biologic.

11. A method of delivering a therapeutic agent, comprising the step of administering to a patient in need an effective amount of the therapeutic agent with the bio-microbur therapeutic delivery platform of claim 1.

12. The method of delivering a therapeutic agent as recited in claim 11, wherein the step of administering comprises orally administering the bio-microbur therapeutic delivery platform and the therapeutic agent to the patient.

13. The method of delivering a therapeutic agent as recited in claim 12, wherein the oral administration of the bio-microbur therapeutic delivery platform and the therapeutic agent comprises delivering the bio-microbur therapeutic delivery platform and the therapeutic agent in a capsule.

14. The method of delivering a therapeutic agent as recited in claim 12, wherein the oral administration of the bio-microbur therapeutic delivery platform and the therapeutic agent comprises delivering the bio-microbur therapeutic delivery platform and the therapeutic agent in a hydrogel.

15. The method of delivering a therapeutic agent as recited in claim 11, wherein the step of administering comprises injecting the bio-microbur therapeutic delivery platform and the therapeutic agent into the patient.

16. The method of delivering a therapeutic agent as recited in claim 15, wherein the injection of the bio-microbur therapeutic delivery platform and the therapeutic agent comprises delivering the bio-microbur therapeutic delivery platform and the therapeutic agent to the patient with at least one type of cell, wherein the bio-microbur therapeutic delivery platform adheres to the at least one type of cell.

17. A method of making the bio-microbur therapeutic delivery platform of claim 1, comprising the steps of:

adding $Mn(CH_3COOH)_2 \cdot 4H_2O$ to $(NH_4)_2S_2O_8$ to form a first solution;

adding sulfuric acid to the first solution to form a second solution;

heating the second solution to form a precipitate of bio-microburs; and extracting and washing the bio-microburs.

18. A method of making the bio-microbur therapeutic delivery platform of claim 1, comprising the steps of:

adding an aqueous solution of $Zn(CH_3COOH)_2 \cdot 2H_2O$ to an aqueous solution of NaOH to form a solution;

heating the solution to form a precipitate of bio-microburs;

washing the bio-microburs; and drying the bio-microburs.

* * * * *